(12) United States Patent
Heil et al.

(10) Patent No.: US 8,943,635 B2
(45) Date of Patent: Feb. 3, 2015

(54) PERSONAL CARE DEVICE

(75) Inventors: Benedikt Heil, Friedberg (DE); Thomas Fritsch, Eppstein (DE); Ingo Vetter, Karben (DE)

(73) Assignee: Braun GmbH, Kronberg (DE)

( * ) Notice: Subject to any disclaimer, the term of this patent is extended or adjusted under 35 U.S.C. 154(b) by 294 days.

(21) Appl. No.: 13/557,241

(22) Filed: Jul. 25, 2012

(65) Prior Publication Data

US 2013/0025078 A1 Jan. 31, 2013

(30) Foreign Application Priority Data

Jul. 25, 2011 (EP) ..................................... 11006100

(51) Int. Cl.
- *A46B 13/02* (2006.01)
- *A61C 17/34* (2006.01)
- *A61C 17/22* (2006.01)

(52) U.S. Cl.
CPC ........... *A61C 17/3436* (2013.01); *A61C 17/221* (2013.01)
USPC ................................ 15/22.1; 15/22.2; 15/22.4

(58) Field of Classification Search
CPC .............................. A46B 13/023; A61C 17/34
USPC ........................................ 15/22.1, 22.2, 22.4
See application file for complete search history.

(56) References Cited

U.S. PATENT DOCUMENTS

| | | | |
|---|---|---|---|
| 5,493,747 A | | 2/1996 | Inakagata et al. |
| 6,140,723 A | * | 10/2000 | Matsui et al. .................... 310/81 |
| 2003/0233877 A1 | | 12/2003 | Grez et al. |
| 2007/0136964 A1 | | 6/2007 | Dawley |
| 2010/0175207 A1 | | 7/2010 | Kraus et al. |

FOREIGN PATENT DOCUMENTS

EP  2 218 559 A1  8/2010

OTHER PUBLICATIONS

International Search Report for PCT/IB2012/053802—dated Dec. 11, 2012.

* cited by examiner

*Primary Examiner* — Randall Chin
(74) *Attorney, Agent, or Firm* — Vladimir Vitenberg

(57) ABSTRACT

A personal care device is disclosed. The personal care device includes an electrically powered driving unit for driving a working implement of the personal care device at a desired speed and/or amplitude and/or frequency; and a control unit for controlling the driving unit in response to load onto the working implement. The control unit includes a detector for detecting an operating parameter of the driving unit responsive to load onto the working implement, and a powering unit for varying the electrical powering of the driving unit in response to a detected change of the value of the operating parameter such that speed and/or amplitude and/or frequency of the working implement is changed from an idling value to an operation value.

16 Claims, 3 Drawing Sheets

PERSONAL CARE DEVICE

CROSS REFERENCE TO RELATED APPLICATIONS

This application is a continuation of International Application No. 11006100.9, filed Jul. 25, 2011, the substance of which is incorporated by reference in its entirety herein.

FIELD OF THE INVENTION

The present disclosure is directed to a personal care device such as an electric toothbrush or shaver.

BACKGROUND OF THE INVENTION

Power-driven personal care devices such as electric toothbrushes or shavers are known. For example, the working implement of an electric toothbrush may include a bristle field arranged on a head that is driven by an electric motor in an oscillating rotation wherein the head may be connected to a motor shaft through a transmission train including gearing structure to transform motor shaft rotation into the desired bristle field movement. In another example, the head of a toothbrush is driven in a vibrating manner wherein the vibrating movement may be achieved by means of a rotating eccentric mass causing vibration of the brush head and the bristle field provided thereon. In still other examples, the heads of electric toothbrushes may be driven by magnetic drive systems effecting oscillating movement of the head by means of applying cyclically varying magnetic fields to a magnetic drive element.

A feature commonly found on electric toothbrushes and other personal care devices is an on/off switch or button which may be actuated to electrically activate or deactivate the driving unit of the device. The primary feature of such a switch is that it remains either in the "on" position or the "off" position until the user manually changes it. When the driving unit is activated prior to the head being placed in the mouth, the bristle field is run at predetermined speed, amplitude and/or frequency intended for operation, which may cause fluid and toothpaste to splatter around and unwanted noise to be generated.

In view of such shortcomings, it is known to provide an electric toothbrush with an automatic mode of operation in which the driving unit is activated when the toothbrush is being used in the mouth, i.e. when the bristle field is pressed against teeth or when the brush head is placed into the mouth. It is known to automatically start the driving unit of a toothbrush when contact to saliva, optionally mixed with toothpaste and water, is detected at the head which is provided with electrical conducting elements that respond to electrical conductivity of fluids present in the mouth. Furthermore, it is known to detect deflection of the toothbrush neck when pressing the head against the teeth and to activate the driving unit when such deflection exceeds beyond a certain predetermined threshold.

Such known automatic mode controls are rather complicated in structure, bulky in size and expensive in realization. The detection sensors for detecting pressure onto the bristle field or the presence of saliva need additional wiring and are detrimental to compact, small-sized designs.

Accordingly, it is desirable to provide an improved personal care device that allows for variation of the working implement speed, amplitude and/or frequency in response to load onto the working implement in a relatively simple manner.

SUMMARY OF THE INVENTION

According to one embodiment, a personal care device is provided. The personal care device includes an electrically powered driving unit for driving a working implement of the personal care device at a desired speed and/or amplitude and/or frequency; and a control unit for controlling the driving unit in response to load onto the working implement. The control unit includes a detector for detecting an operating parameter of the driving unit responsive to load onto the working implement, and a powering unit for varying the electrical powering of the driving unit in response to a detected change of the value of the operating parameter such that speed and/or amplitude and/or frequency of the working implement is changed from an idling value to an operation value.

According to another embodiment, a personal care device is provided. The personal care device includes an electrically powered driving unit for driving a working implement of the personal care device at a desired speed and/or amplitude and/or frequency; and a control unit for controlling the driving unit such that the working implement is driven with an idling value of speed and/or amplitude and/or frequency when the personal care device is switched on. The control unit includes a detector for detecting an operating parameter of the driving unit, which operation value is responsive to load onto the working implement, and a powering unit for varying the electrical powering of the driving unit in response to a detected value of the operating parameter representing a load that is above a certain threshold load such that speed and/or amplitude and/or frequency of the working implement is changed from the idling value to an operation value, wherein the idling value is at least about 5% of the operation value but not higher than about 75% of the operation value.

These and other features, aspects and advantages of specific embodiments will become evident to those skilled in the art from a reading of the present disclosure.

BRIEF DESCRIPTION OF THE DRAWINGS

The embodiments set forth in the drawings are illustrative in nature and not intended to limit the invention defined by the claims. The following detailed description of the illustrative embodiments can be understood when read in conjunction with the following drawings, where like structure is indicated with like reference numerals and in which:

DETAILED DESCRIPTION OF THE INVENTION

Figure 1:
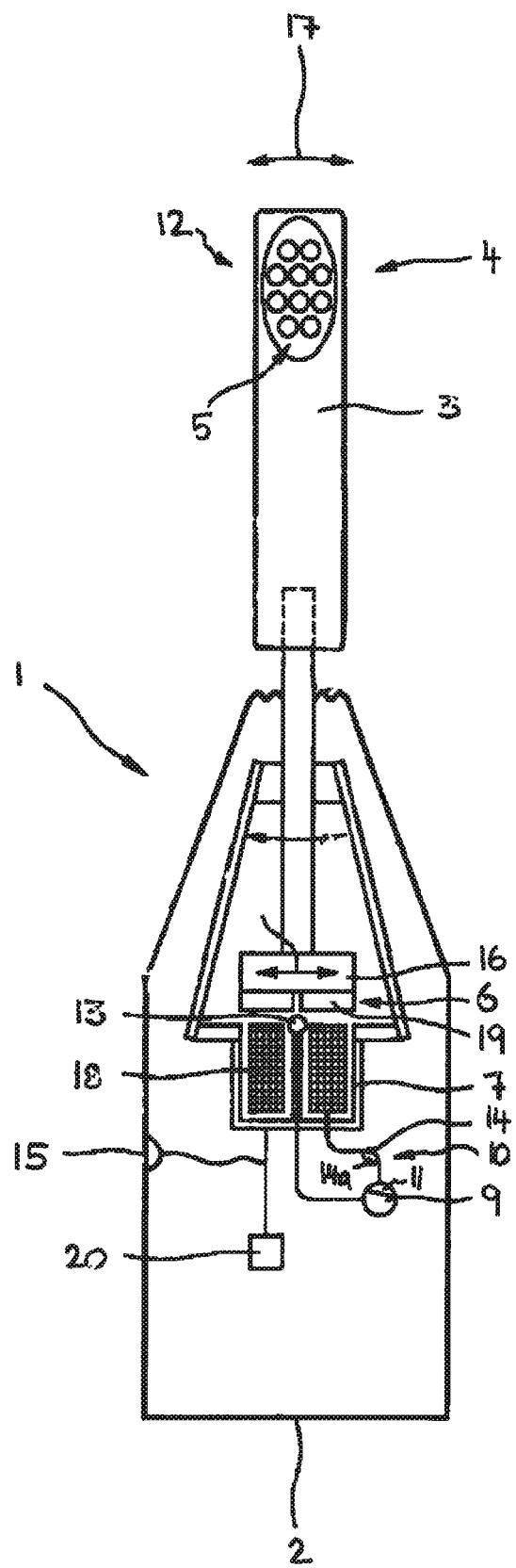
FIG. 1: A simplified, partly cross-sectional view of a personal care device realized as an electric toothbrush according to an example embodiment.

The following text sets forth a broad description of numerous different embodiments of the present disclosure. The description is to be construed as exemplary only and does not describe every possible embodiment since describing every possible embodiment would be impractical, if not impossible. It will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims. All publications and patents cited herein are incorporated herein by reference.

In accordance with at least one aspect of the present disclosure, load onto a working implement of a personal care device is determined through detecting an operating parameter of a driving unit responsive to load onto the working implement, where the variation of the speed and/or amplitude and/or frequency value may be triggered either by the absolute value of the operating parameter or by a detected change of the operating parameter.

In accordance with at least another aspect of the present disclosure, speed and/or amplitude and/or frequency of the working implement are changed from an idling value to an operation value, in one example, an operation value that is increased over the idling value, in response to a change of an operating parameter of the driving unit responsive to load onto the working implement.

According to an embodiment, the operating parameter of the driving unit that is monitored to determine load onto the working implement includes speed and/or amplitude and/or frequency of the driving unit. The detector of the control unit may include a speed determining unit for determining a change in speed and/or amplitude and/or frequency of the driving unit, in particular a decrease of these parameters. The powering unit may be arranged to adapt the electric powering such that speed and/or amplitude and/or frequency of the working implement is changed (for example, increased) from an idling value to an operation value upon determination of a decrease in speed and/or amplitude and/or frequency of the driving unit when supplying electric power to the driving unit in an idling mode. The speed determining unit can have different embodiments, wherein a speed sensor may be provided for sensing rotational speed of a motor shaft or a transmission shaft or another element of the drive train. Additionally or alternatively, the speed determining unit may include electronic circuitry associated with the driving unit and/or a power supply unit supplying electric power to the driving unit to determine speed and/or amplitude and/or frequency of the driving unit in an electronic manner on the basis of current signals present in or supplied to the driving unit.

In an embodiment, where speed and/or amplitude and/or frequency of the driving unit is detected as operating parameter to determine load on the working implement, it may be assumed that speed and/or amplitude and/or frequency of the driving unit will at least temporarily show a change, in particular a decrease, when a load is applied at the working implement, for example, by means of pressing the bristle field against teeth.

Alternatively or additionally, a characteristic electric parameter may be detected as operation parameter of the driving unit to determine load onto the working implement and variations thereof. More particularly, the detector of the control unit may include a determining unit for determining a variation of an electric operation parameter of the driving unit responsive to load onto the working implement. The powering unit may be adapted such that electric powering is varied to increase speed and/or amplitude and/or frequency of the working implement to the desired operation value upon determination of a variation of the electric operation parameter indicative of a certain load onto the working implement.

Different electric operation parameters may be detected to determine load onto the working implement. In an embodiment, current consumption of the driving unit may be monitored as operating parameter and may be used for triggering a change (i.e. an increase or a decrease) of the speed and/or amplitude and/or frequency of the working implement to the desired value thereof. The detector may include a current detector for detecting current consumption of the driving unit. The control unit may be adapted such that electric powering of the driving unit is varied to change speed and/or amplitude and/or frequency of the working implement to the desired operation value upon determination of a specific current consumption and/or increase thereof. Using the current consumption of the driving unit for determining load onto the working implement allows for simple structure of the detector. Basically, a current meter or voltage meter may suffice.

Current consumption of the driving unit may be analyzed in different ways. Current consumption may be compared to a predetermined absolute value and, when current consumption exceeds such predetermined absolute value, speed and/or amplitude and/or frequency of the working implement may be increased to the desired operation value. Alternatively or additionally, current consumption may be monitored and variations of the current consumption of the driving unit may be compared to at least one specific variation characteristic which may include slope and/or the amount of variation. For example, if the variation of the current consumption exceeds a certain slope, i.e. the amount of variation per time, and/or a specific amount of increase, the control unit may vary electric powering of the driving unit to increase the speed and/or amplitude and/or frequency of the working implement to the desired operation value.

Additionally or alternatively, the detector of the control unit may include an electronic detection unit for detecting deviations in amplitude, pulse width and/or progression of current and/or voltage present in the driving unit or an element thereof or a component connected thereto, from the current and/or voltage signal of the electric power supplied to the driving unit. For example, it may be detected if the current signal in a coil of a motor of the driving unit follows a predetermined signal in terms of signal shape, amplitude, pulse width and/or offset in time in a sufficient close manner. When deviations exceed a predetermined threshold, the control unit may assume there is sufficient load onto the working implement going beyond the unloaded state so that the operation state may be switched from idling mode to operation mode.

The control unit may include an idle powering unit for controlling the driving unit in an idle mode providing for an idling value of speed and/or amplitude and/or frequency of the working implement which idling value may be reduced in comparison to the desired operational value.

Upon detection of load onto the working implement, the idle powering unit may be deactivated so that the driving unit does not return to idle mode when load onto the working implement falls below a certain value or the working implement is completely unloaded. Alternatively, the idle control may be activated again when the control unit detects the load onto the working implement falling under a certain lower limit.

The idle powering unit may be operatively connected to an on/off switch to activate the idle powering unit upon switching on the driving unit.

Generally, a personal care device as proposed includes a control unit that controls a driving unit of the personal care device, which driving unit drives a working implement of the personal care device at a certain speed and/or amplitude and/or frequency. The control unit includes a detector for detecting an operation parameter of the personal care device that is indicative of the load that is applied at the working implement. In one embodiment, the control unit may be arranged to change the powering of the driving unit in dependence on the detected absolute value of the operating parameter, i.e. to change the powering of the driving unit when the operating parameter is above or below a certain first (second, third, . . . ) threshold value. In another embodiment, the control unit may be arranged to change the powering of the driving unit in dependence of a certain change of the operating parameter, for example, a characteristic decrease of the operating parameter indicative of a certain applied load. The control unit may in particular be arranged to power the driving unit such that speed and/or amplitude and/or frequency of the working implement is at an idling value if the load applied at the working implement is below a first threshold load value (and thus above or below a first threshold value of the operating parameter). The control unit may then be arranged to vary the powering of the driving unit to achieve a certain operation value of the speed and/or amplitude and/or frequency of the working implement when the operating parameter indicates a load at or above the first threshold load value. The control unit may in one embodiment be arranged to vary the powering again when the load applied at the working implement is at or above a second threshold load value or in some embodiments the speed and/or amplitude and/or frequency may be set to zero or essentially zero when a load at or above the second threshold load value is detected. In some embodiments, the control unit is arranged to power the driving unit such that the idling value of the speed and/or amplitude and/or frequency is achieved when the personal care device is switched on.

FIG. 1 shows an example embodiment of a personal care device 1 in accordance with the present disclosure, where the personal care device may be an electric toothbrush. As shown by FIG. 1, a personal care device 1 may include a handle 2 formed by an elongated hollow casing within which other portions of the personal care device may be disposed such as a battery, a driving unit 6 including a motor 7 or a control unit 9 for controlling the motor 7. Furthermore, the personal care device 1 includes a functional element 4, for example, a brush head, which is connected to the handle 2 by means of a neck 3. The neck may be detachably connected to a driving element 16 that may be driven by motor 7 so that the functional element 4 forms an exchangeable attachment of the personal care device 1. As shown by FIG. 1, the functional element 4 here comprises a bristle field 5 which includes a plurality of bristles that may be arranged in any known manner. However, the functional element 4 may include alternatively or additionally cleaning elements such as needle-like interdental cleaning elements, sponge-like massaging elements, polishing elements or other oral treatment elements. In the shown example embodiment, the functional element 4 forms a working implement 12 in accordance with the present disclosure as the whole functional element 4 is driven into an oscillatory motion having an amplitude, a frequency and a speed. In another example embodiment, the functional element may comprise a carrier element movably mounted at the functional element, which carrier element may carry a bristle field and which carrier may be driven into an oscillatory motion. In such an embodiment, the carrier element carrying the bristle field forms a working implement in accordance with the present disclosure.

The functional element 4 can be driven to move in an oscillating manner as indicated by arrow 17. The aforementioned driving element 16 is supported pivotably within handle 2 to swing to and fro. Consequently, the neck 3 connected to the driving element 16 rotates in an oscillating manner about an axis extending substantially perpendicular to the longitudinal extension of the neck 3. The motor 7 may include coils 18 for generating a magnetic field that interacts with magnets 19 provided on the driving element 16.

To provide the motor 7 with electric power, the personal care device 1 may include a power supply 20 which may include batteries received within handle 2 and/or a mains adapter to be connected to an external power supply.

A control unit 9 controls the motor 7 and supplies driving signals to the coils 18 to generate a cyclically varying magnetic field to drive the driving element 16. In some embodiments, the motor is a DC motor, in other embodiments, a resonant motor may be utilized.

Control unit 9 further includes a detector 10 to detect operating parameters of the driving unit 6, the detector 10 may include speed detecting means 13 for detecting speed, amplitude and/or frequency of the movement of the driving element 16. Furthermore, the detector 10 may include a determining unit 14 for determining at least one electric operation parameter of the motor 7, which determining unit 14 may include a current detector 14a for detecting current consumption of the driving unit 6 and furthermore, electronic detection unit for detecting deviations of the current and/or voltage signal present in driving unit 6 from a current and/or voltage signal of the electric power supply to the driving unit in terms of amplitude, pulse width and/or frequency and/or signal shape.

Figure 2:
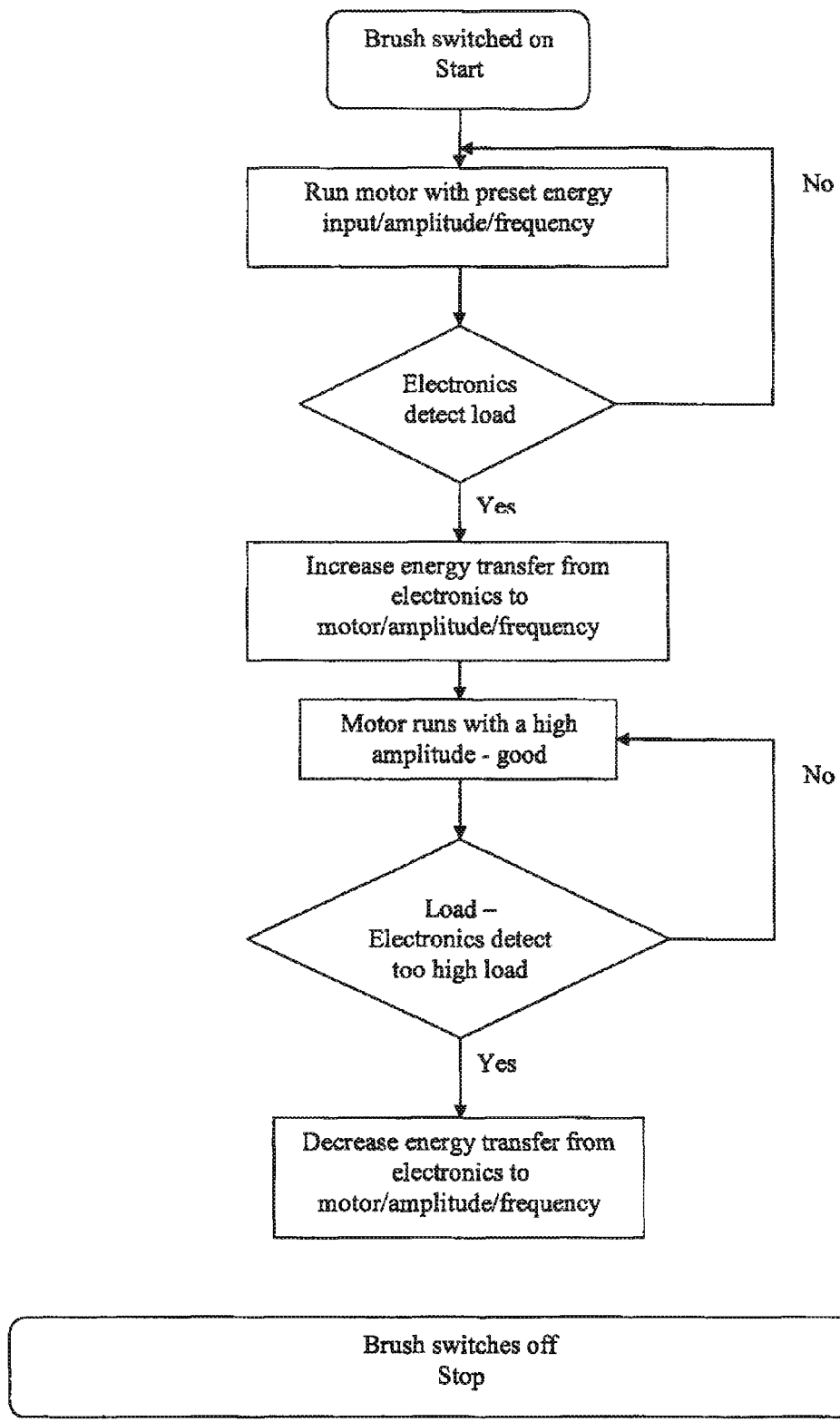
FIG. 2: a flow chart showing the control steps performed by the control unit of the personal care device of FIG. 1.

As shown by FIG. 2, a personal care device 1 may be provided with different operation modes including an idle mode and a regular operation mode. When the personal care device 1 is started by means of pushing or pressing an on/off switch 15, the motor 7 is energized to drive the functional element 4. Upon starting the driving unit 6, the control unit 9 may start in an idle mode wherein the motor 7 is run with a reduced preset energy input such that the driving element 16 and thus the functional element 4 executes a movement having at least one of a reduced amplitude or reduced frequency so that at least one of these idle parameters is smaller than an amplitude or an frequency used during regular teeth-cleaning operation.

Figure 3:
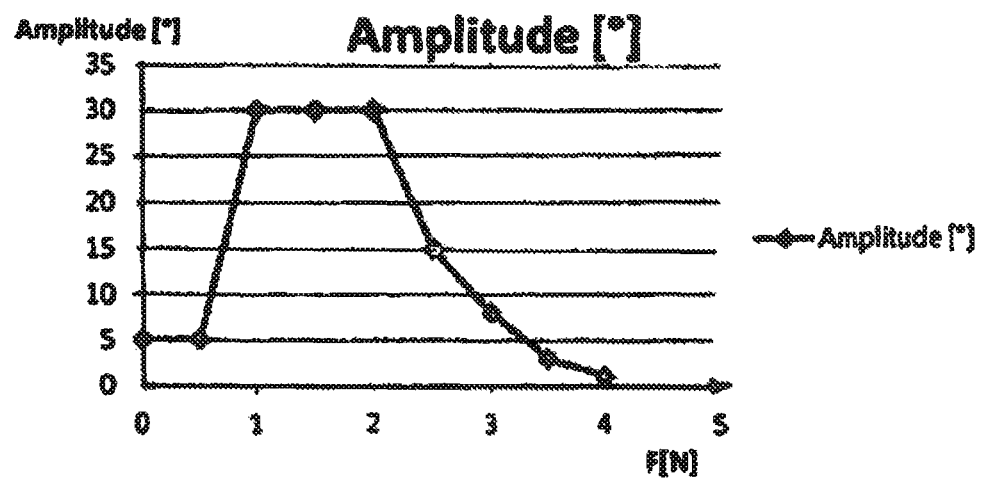
FIG. 3: a functional diagram showing the amplitude of the working implement over load applied to the working implement.

As shown by FIG. 3, the idle mode may provide for an amplitude (for example, angular deflection) of greater than 0°, but, for example, less than 15°, wherein FIG. 3 shows an idle amplitude of 5°. Typically, a low amplitude or a low speed is desirable for the idle mode insofar as a small amplitude (or a low speed) provides for a user-perceivable signal that the personal care device is switched on (i.e. that the personal care device is operational). Further, a substance such as water or toothpaste that may be applied to the working implement is less likely to be splattered around at a low amplitude/low speed and also the noise generated by the personal care device tends to be lower than the noise generated in a standard operation mode. Generally, the amplitude in terms of an angular displacement may be chosen to lie in a range of between about 0.5 degrees to about 10 degrees, or in other terms, the low amplitude may be chosen to lie within a range of between about 5% to about 75% of the desired operation amplitude. In an embodiment in which the working implement is driven into a linear oscillation, the low amplitude in idle mode may be chosen to lie in a range of between about 0.05 mm to about 0.5 mm or again may be chosen to lie within a range of between about 5% to about 75% of the desired operation amplitude. Operational amplitude may be chosen to lie in a range of between about 2 degrees to about 90 degrees or between about 0.2 mm to about 5 mm. The operation amplitude may depend on the concrete personal care device. In some embodiments, a shaver may benefit from larger amplitudes such as operation amplitudes of 2 mm or higher (or 30 degrees or higher angular deflection), while a toothbrush may be restricted to smaller operation amplitudes to avoid user discomfort, thus operation amplitudes of below 2 mm (or below 30 degrees angular deflection). Additionally or alternatively to the change of the amplitude from an idle amplitude value to an operation amplitude value, the frequency and/or the speed at which the working implement moves may be changed. The idle frequency (for an oscillatory motion this parameters is inherently coupled with the speed parameter) may be chosen to lie in a range of between about 1 Hz to about 50 Hz, while the operational frequency may be chosen to lie in a range of between about 20 Hz to about 1,000 Hz. As an example, for an electric toothbrush the idle frequency value may be chosen to lie in a range of between about 1 Hz and about 30 Hz and the operational frequency value may be chosen to lie in a range of between about 50 Hz to about 300 Hz.

During such initial idle mode, the electronic control unit 9 detects at least one of the aforementioned operation parameters of the driving unit 6, which operating parameters are selected from the group consisting of speed, amplitude, frequency, current consumption and characteristics of the driving signal and/or the response signal in the coils 18 to determine if load is applied to the bristle field 5. If a load at or above a certain first threshold load value is applied to bristle field 5, at least one of speed, amplitude or frequency will change (usually increase) in comparison to the respective idling value under a no load condition. For sake of completeness it is again stated that the control unit detects an operation parameter of the driving unit that is indicative of the load applied at the working implement. As such, the operating parameter may have a value above or below a certain first threshold value to indicate that the load applied at the working implement is above a first threshold load value. Upon detection of a certain load by means of detector 10, the control unit 9 may switch the driving unit 6 to be operated in a second operation mode which may be a regular operation mode, for example, a regular teeth-cleaning mode in case that the personal care device is realized as an electric toothbrush. As shown by FIG. 2, the energy transfer from the electronics to the motor 7 is then increased so that the amplitude and/or speed and/or frequency of the driving element 16 and therefore of the working implement 12 is increased to an operation value. For example, the amplitude may be increased by at least about 10° in comparison to the idle mode, wherein FIG. 3 shows an increase to an operation amplitude of about 30°. However, other amounts of increase are possible as has been discussed.

According to an embodiment, the amplitude of the working implement 12 is increased from an idle amplitude value to an operation amplitude value, whereas the frequency may be kept constant to avoid irritation of the users due to the changes in the device sound.

After having switched the driving unit 6 to the operation mode, idle mode control may be resumed upon detection of an unloaded condition. However, alternatively such idle mode control may not be resumed after having switched the driving unit 6 to the regular operation mode even if the load onto the bristle field 5 drops to zero.

As shown by FIG. 3, the control unit 9 may include an overload control mode, wherein the amplitude is again reduced when the detector 10 detects an operation parameter indicative of an excessive load onto the working implement (i.e. when the load is at or above a second threshold load value). Depending on the working implement and the personal care function to be carried out, it also would be possible to reduce frequency and/or speed upon detection of such overload condition. As shown by FIG. 3, the reduction of the amplitude may depend on the amount of overload. The more the load increases, the more the amplitude may be reduced, wherein the amplitude may be reduced to zero, i.e. the driving unit 6 may be stopped completely when load reaches a certain value beyond useful regular load values.

Control of the amplitude may use a stored reference profile for the amplitude as shown in FIG. 3. According to a more sophisticated embodiment, the control unit 9 may include an input unit (for example, a touch sensitive screen, one or several sensor switches, one or several knobs etc.) to input such reference profile to allow for modification of the stored reference profile and/or input of a completely new custom-made reference profile.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed:

1. A personal care device comprising:
an electrically powered driving unit for driving a working implement of the personal care device at a desired speed and/or amplitude and/or frequency; and
a control unit for controlling the driving unit in response to load onto the working implement;
wherein the control unit includes a detector for detecting an operating parameter of the driving unit responsive to load onto the working implement, and a powering unit for varying the electric powering of the driving unit in response to a detected change of the value of the operating parameter such that speed and/or amplitude and/or frequency of the working implement is changed from an idling value to an operation value, and wherein the idling value is in the range of from about 5% to about 75% of the operation value.

2. The personal care device according to claim 1, wherein the detector includes a speed determining unit for determining a change in speed and/or amplitude and/or frequency of the driving unit, wherein the powering unit is adapted such that the electric powering is varied to increase speed and/or amplitude and/or frequency of the working implement to the desired operation value upon determination of a specific decrease in speed and/or amplitude and/or frequency of the driving unit.

3. The personal care device according to claim 1, wherein the control unit is arranged to vary the electric powering of the driving unit when the operation parameter indicates a load above a first threshold value.

4. The personal care device according to claim 1, wherein the detector includes a determining unit for determining a variation of an electric operation parameter of the driving unit, wherein the powering unit is adapted such that electric powering of the driving unit is varied to increase speed and/or amplitude and/or frequency of the working implement to the desired operation value upon determination of a specified variation of the electric operation parameter.

5. The personal care device according to claim 1, wherein a determining unit includes a current detector for detecting current consumption of the driving unit, wherein the powering unit is adapted such that electric powering of the driving unit is varied to increase speed and/or amplitude and/or frequency of the working implement to the desired operation value upon determination of a specific current consumption and/or increase thereof.

6. The personal care device according to claim 1, wherein a determining unit is arranged to compare the current consumption to a predetermined absolute value and/or to compare a variation in current consumption to at least one specific variation characteristic, wherein the driving unit is arranged to increase speed and/or amplitude and/or frequency of the working implement when the current consumption exceeds the predetermined absolute value and/or the variation in current consumption exceeds at least one variation characteristic.

7. The personal care device according to claim 1, wherein the detector includes an electronic detection unit for detecting deviations of current and/or voltage present in the driving unit from a current and/or voltage signal of the electric power supplied to the driving unit in terms of amplitude and/or pulse width and/or frequency and/or signal shape.

8. The personal care device according to claim 1, wherein the control unit includes an idle powering unit for controlling the driving unit in an idle mode providing for an idling value of speed and/or amplitude and/or frequency of the working implement, the idle powering unit being operatively connected to an on/off switch for switching on/off of the driving unit to activate the idle powering unit upon switching on the driving unit.

9. The personal care device according to claim 8, wherein the idle powering unit is deactivated once the detector detects a change of the monitored operating parameter in response to load onto the working implement.

10. The personal care device according to claim 1, wherein the control unit provides for at least two different operation modes including an idle mode wherein the driving unit is run with a reduced preset energy input and a regular operation mode wherein the driving unit is run with an energy input larger than the reduced preset energy input of the idle mode, wherein the control unit automatically selects the idle mode upon starting the driving unit.

11. The personal care device according to claim 1, wherein the control unit is provided with storing means for storing a reference profile which includes at least one predetermined value selected from the group consisting of speed, amplitude and frequency related to specific load values and/or operating parameter values indicative thereof, and wherein the control unit is arranged to use the stored reference profile to determine speed and/or amplitude and/or frequency for different load conditions.

12. The personal care device according to claim 11, wherein the control unit is provided with an input unit for entering and/or modifying the stored reference profile.

13. The personal care device according to claim 1, wherein the driving unit comprises a resonant motor.

14. The personal care device according to claim 1, wherein the personal care device is an electric toothbrush.

15. A personal care device comprising:
an electrically powered driving unit for driving a working implement of the personal care device at a desired speed and/or amplitude and/or frequency; and
a control unit for controlling the driving unit such that the working implement is driven with an idling value of speed and/or amplitude and/or frequency when the personal care device is switched on;
wherein the control unit includes a detector for detecting an operating parameter of the driving unit, wherein an operation value of the operating parameter is responsive to load onto the working implement, and a powering unit for varying the electrical powering of the driving unit in response to a detected value of the operating parameter representing a load that is above a certain threshold load such that speed and/or amplitude and/or frequency of the working implement is changed from the idling value to the operation value, wherein the idling value is at least about 5% of the operation value but not higher than about 75% of the operation value.

16. The personal care device according to claim 15, wherein the personal care device is an electric toothbrush.

* * * * *